United States Patent [19]

Jones et al.

[11] Patent Number: 4,743,663

[45] Date of Patent: May 10, 1988

[54] AROMATIC OLIGOMERS

[75] Inventors: Michael E. B. Jones, Chester; John G. Carey, Appleton, both of England

[73] Assignee: Imperial Chemical Industries PLC, London, England

[21] Appl. No.: 733,920

[22] Filed: May 14, 1985

[30] Foreign Application Priority Data

May 14, 1984 [GB] United Kingdom ............... 8412264
Jan. 28, 1985 [GB] United Kingdom ............... 8502040

[51] Int. Cl.⁴ .................. C08F 283/00; C08L 283/12; C08G 8/04; G03C 1/727
[52] U.S. Cl. ................................ 525/539; 525/451; 525/521; 525/502; 528/148; 522/144; 522/181; 430/287; 430/285
[58] Field of Search ............... 525/539, 451, 521, 502; 528/148; 430/287, 285; 522/144, 181

[56] References Cited

U.S. PATENT DOCUMENTS

| | | | |
|---|---|---|---|
| 3,025,260 | 3/1962 | Luck et al. ............... | 528/148 X |
| 4,252,888 | 2/1981 | Rohloff ..................... | 522/181 X |
| 4,379,826 | 4/1983 | Economy .................. | 430/141 |
| 4,379,866 | 4/1983 | Henry, Jr. et al. . | |
| 4,435,496 | 3/1984 | Walls et al. .............. | 430/285 |
| 4,530,992 | 7/1985 | Jones ........................ | 528/232 |

FOREIGN PATENT DOCUMENTS 0059649 9/1982 European Pat. Off. .
0112650 7/1984 European Pat. Off. .
1408265 10/1975 United Kingdom .

Primary Examiner—Paul R. Michl
Assistant Examiner—Cynthia Hamilton
Attorney, Agent, or Firm—Cushman, Darby & Cushman

[57] ABSTRACT

Compositions comprising an oligomer which (a) on average comprises at least one in-chain residue of the general formula

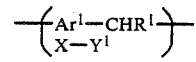

wherein $Ar^1$ is an aromatic group, $R^1$ is hydrogen or a hydrocarbyl group, X is a group which activates $Ar^1$ to electrophilic attack, and $Y^1$ is an organic residue bearing a carboxyl substituent; and (b) has one or more pendant and/or terminal acyloxymethyl groups are described. They may be used in dental, electronic and electrical applications.

13 Claims, No Drawings

AROMATIC OLIGOMERS

This invention relates to compositions comprising aromatic oligomers, to the preparation of such oligomers, to resins prepared from such compositions and to filled and/or fibre-reinforced articles comprising such resins.

The reaction of certain aromatic compounds with certain aldehydes, particularly formaldehyde, in the presence of a carboxylic acid and a strong acid under defined conditions to give oligomers, and the conversion thereof into resins having useful properties, e.g., glass transition temperatures in the range of 80° C. to 290° C., depending on the functionality and molecular weight of the oligomer, moreover, the resins may form the matrices for useful fibre-reinforced composites, particularly where the fibre is carbon fibre, is described in European patent specification No. 0,112,650A, the disclosure in which specification is incorporated herein by way of reference.

We have now found (a) that certain aromatic compounds bearing a carboxyl substituent indirectly attached to the aromatic nucleus thereof may be used in the aforesaid reaction, and (b) certain oligomers prepared therefrom are soluble in dilute alkali solution, and on polymerisation afford resins which are, surprisingly, resistant to hot concentrated alkali solution.

According to the present invention there is provided a composition comprising an oligomer, which may be linear or branched, which (a) comprises on average at least one in-chain residue of the general formula

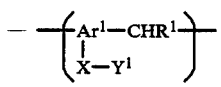     I and (b) has one or more pendant and/or terminal acyloxymethyl groups.

In general formula I,
$Ar^1$ is an aromatic group or a substituted aromatic group;
$R^1$ is hydrogen or a hydrocarbyl group;
X is a group which activates $Ar^1$ to electrophilic attack; and
$Y^1$ is an organic residue bearing a carboxyl substituent.

It is often preferred that the oligomer comprises, in addition to at least one residue of general formula I, one or more residues of general formula

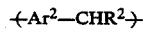     II wherein
$Ar^2$, which may be the same as or different from $Ar^1$, is an aromatic group or a substituted aromatic group; and
$R^2$, which may be the same as or different from $R^1$, is hydrogen or a hydrocarbyl group.

The presence of one or more residues of the general formula II in oligomers used in compositions according to the present invention allows the functionality, as hereinafter defined, of the oligomer to be increased and affords a means of adjusting the sensitivity to base of the resin obtained on curing of the oligomer.

Whilst we do not exclude the possiblity that the aromatic group $Ar^1$ may have a plurality of phenyl rings, e.g. biphenyl, or fused phenylene rings, e.g. naphthalene, preferably it is mononuclear.

The aromatic group $Ar^2$ may be mononuclear, e.g. as in phenylene; or fused polynuclear, e.g. as in naphthalene or anthracene; or preferably has the structure $-\phi-Y^2-\phi-$. In $-\phi-Y^2-\phi-$, $\phi$ is the phenylene group and $Y^2$ is a direct link between the two phenylene groups; or a divalent residue which includes one or more in-chain atoms, each of which atoms may be carbon or a hetero atom and may have one or more atoms appendant thereto, e.g., $-O-$, $-S-$, $-CH_2-$, or a substituted derivative of $-CH_2-$, e.g. $-(CH_3)_2-$, $-CH_2CH_2-$, or

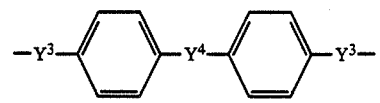

where $Y^3$, each of which may be the same or different, is a group which activates the aromatic nucleus to electrophilic attack, e.g., $-O-$ and $-S-$, and $Y^4$ is a group which deactivates the aromatic nucleus to electrophilic attack, e.g. $-SO_2-$ and $-CO-$.

Oligomers used in compositions according to the present invention in which $Ar^2$, where present, has a plurality of phenyl groups, e.g. diphenyl oxide, or fused phenylene rings often polymerise to form resins faster than homooligomers in which $Ar^2$ is absent.

Where oligomers used in compositions according to the present invention comprise repeat units

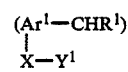

and $(Ar^2-CHR^2)$ the molar ratio of $Ar^2:Ar^1$ is preferably less than 6:1 and more preferably is between 3:1 and 1:3. Where the molar concentration of the repeat unit

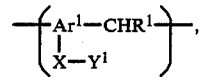

expressed as a percentage of the total molar repeat units, is less than about 25% there is a tendency for the oligomer to be insoluble in dilute base. The molar ratio of $Ar^2:Ar^1$ is often chosen such that the oligomer is readily soluble in dilute, for example about 2% w/w, aqueous carbonate solution and the resin prepared by the curing thereof is resistant to attack by hot alkali solution.

Substituents which may be present on the aromatic groups $Ar^1$ and $Ar^2$ include interalia lower alkyl groups having up to five carbon atoms, e.g. methyl and ethyl; lower alkoxy groups e.g. methoxy; and halo groups, e.g. chloro.

Where the groups $R^1$ and $R^2$ are hydrocarbyl groups they may be aryl groups, e.g. phenyl; alkaryl groups, e.g. tolyl; aralkyl groups, e.g. benzyl; or preferably alkyl groups having up to six carbon atoms, e.g. methyl or ethyl. We do not exclude the possiblity that $R^1$ and $R^2$ may bear one or more suitable substituents, e.g. halo groups. Preferably, however, $R^1$ and $R^2$, where $R^2$ is present, are hydrogen atoms.

X may be inter alia $-NH-$, $-S-$, or preferably $-O-$.

It is often preferred that the organic residue of which $Y^1$ is comprised is a hydrocarbyl residue, e.g. an aromatic chain or an alkylene chain or preferably a phenylene group or more preferably a methylene group. Where the organic residue comprises a plurality of carbon atoms it is often preferred that the carboxyl group is attached to the carbon atom distant the group X. Where the organic residue comprises a plurality of carbon atoms we do not exclude the possibility that it may contain one or more in-chain or pendant heteroatoms, e.g.

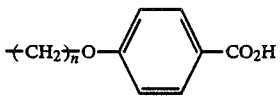

As a particularly preferred example of

may be mentioned

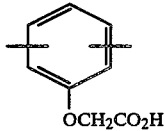

As a particularly preferred example of $Ar^2$ may be mentioned

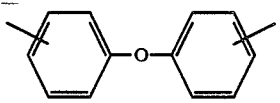

It will be appreciated that where oligomers used in compositions according to the present invention comprise groups of the general formula

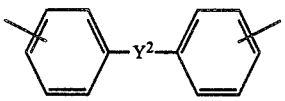

the groups —$CHR^1$— and —$CHR^2$— may both be attached to the aromatic rings at positions para to $Y^2$ or one may be attached at a position on one aromatic ring which is para to $Y^2$ and the other may be attached at a position of the other aromatic ring which is ortho to $Y^2$.

The acyl portion of the acyloxymethyl groups in oligomers used in compositions according to the present invention may be derived from inter alia an aliphatic carboxylic acid, an aromatic carboxylic acid, or preferably a polymerisable olefinically unsaturated carboxylic acid or a substituted derivative thereof.

As examples of suitable olefinically unsaturated carboxylic acids from which the aforesaid acyloxymethyl groups may be derived may be mentioned inter alia ethacrylic, crotonic, angelic, cinnamic, maleic, oleic and linoleic acids or preferably acrylic or methacrylic acid.

It will be appreciated that the functionality and particularly the ratio of number average molecular weight to weight average molecular of oligomers used in compositions according to the present invention will affect inter alia the viscosity and softening point of the oligomers and the mechanical properties of the cured resins prepared therefrom. It is often preferred that the functionality is between 1.5 and three. The skilled man by simple experiment will be able to determine satisfactory average molecular weight ratio/functionality combinations for the oligomers to achieve a desired combination of properties.

By "functionality" we mean the number of acyloxymethyl groups per oligomer molecule.

Where oligomers used in compositions according to the present invention have pendant and/or terminal acyloxymethyl groups in which the acyl group is derived from a polymerisable olefinically unsaturated carboxylic acid they may be copolymerised with a suitable polymerisable olefinically unsaturated comonomer, e.g. an acrylate or methacrylate, or homopolymerised.

Polymerisation may be effected by any of the techniques conventionally used in the addition polymerisation of polymerisable olefinically unsaturated monomers. However, free radical initiation is preferred. Application of heat may assist the polymerisation although by suitable choice of catalyst it is possible to effect polymerisation at or near ambient temperature.

Polymerisable olefinically unsaturated comonomers which may be used in admixture and with which the oligomers may be copolymerised include vinyl esters, aromatic vinyl compounds, vinyl nitriles and N-aryl maleimides.

Suitable vinyl esters include, for example, vinyl acetate or preferably esters of acrylic and methacrylic acids, which esters may have one or more ester groups, e.g. methyl, cyclohexyl, n-hexyl, and tetrahydrofurfuryl acrylates and methacrylates, ethylene glycol acrylates and meathacrylates, di- and triethylene glycol acrylates and methacrylates, and pentaerythritol triacrylate. As examples of suitable aromatic vinyl compounds may be mentioned inter alia styrene and derivatives thereof, e.g. alpha-methyl styrene, and vinyl toluene. Suitable vinyl nitrile compounds include inter alia acrylonitrile and derivatives thereof, e.g. methacrylonitrile. A suitable N-aryl maleimide is N-phenyl maleimide.

Where compositions according to the present invention comprise an oligomer and a polymerisable olefinically unsaturated comonomer the weight ratio of the oligomer to the said comonomer is typically in the range from 1:19 to 19:1. The quantity of polymerisable olefinically unsaturated comonomer which is used will depend on inter alia the viscosity which is required in the composition and on the mechanical properties which are required in the cured resin prepared therefrom. Compositions according to the present invention in which the pendant and/or terminal acyloxymethyl groups comprise an acyl group which is derived from a polymerisable olefinically unsaturated carboxylic acid may be used as dental materials, for example as adhesives, and bonding agents, e.g. to improve the adhesion of dental filling materials to inter alia the dentin and/or enamel, which may be etched or unetched of teeth, or as the matrix in filling materials.

Where compositions according to the present invention are used in or as dental materials, curing thereof is preferably effected by a visible light curing technique using a -photo-initiator system, for example as disclosed in British patent specification No. 1408265, or preferably in European patent specification No. 0,059,649A, the disclosures in which specifications are incorporated herein by way of reference.

Dental products prepared from compositions according to the present invention often adhere more firmly to teeth than the cured products prepared from dental materials which are disclosed and claimed in our aforesaid European patent specification.

Compositions according to the present invention in which the pendant and/or terminal acyloxymethyl groups comprise an acyl group which is derived from a polymerisable olefinically unsaturated carboxylic acid may be used in electronic or electrical applications, for example in photoresists, e.g. non-strippable dry film resists, and in solder masks. They may be used in reprographic processes, e.g. in the preparation of printing plates. They may be used as abrasion resistant surface coatings, particularly when in admixture with a particulate filler.

Where compositions according to the present invention are used in the preparation of photoresists they contain a suitable photoiniator system. As examples of such systems can be mentioned inter alia (a) mixtures of Michler's ketone and benzil or preferably benzophenone, typically in a weight ratio of about 1:4; (b) mixtures of amines and ketones as disclosed in EP No. 90493A, e.g. camphorquinone or fluorenone and N,N-dimethylaminoethyl methacrylate, typically in a weight ratio of about 1:1, (c) the coumarin-based photoinitiator systems described in U.S. Pat. No. 4,289,844, (d) combinations of hexaarylbisimidazoles and leuco dyes, (e) cyclohexadienone-leuco dye systems described in U.S. Pat. No. 4,241,869, or (f) systems based on dimethoxyphenylacetophenone (benzil dimethyl ketal) and/or diethoxyacetophenone.

Where a composition according to the present invention, in the form of a layer, is cured in an imagewise fashion by exposure, in the presence of a suitable photoinitiator system, to electromagnetic radiation, e.g. in the preparation of a photoresist, the uncured portion of the composition may be removed by dissolution in a dilute aqueous solution of a suitable base. Surprisingly, the cured portions, particularly where they have been subjected to a thermal post-cure, are resistant to exposure to hot, say about 80° C., concentrated alkali solutions, e.g. at pH 11-12, for several hours.

Whilst we do not exclude the possibility that the aforesaid suitable base may be an organic amine, for example having a base-ionisation constant greater than about $1 \times 10^{-6}$, e.g. benzylamine or dimathylamine or triethylamine, it is preferred that the base is inorganic, e.g. ammonia, borax, a phosphate or preferably an alkali metal hydroxide or the base-reacting alkali metal salts of weak acids, e.g. sodium carbonate or bicarbonate.

By "dilute" we mean a concentration of up to a few percent weight/weight, e.g. 2%, or up to a few molar, e.g. 1M.

Methods suitable for preparing photoresists, e.g. dry-film resists, from compositions according to the present invention are more fully described in our aforesaid European patent specification No. 0,112,650A.

According to a further aspect of the present invention there is provided a process for the preparation of a photoresist which process comprises the steps of
(i) preparing a layer which comprises a composition according to the present invention;
(ii) exposing the layer imagewise to suitable electromagnetic radiation; and
(iii) treating the layer with a dilute solution of base to remove the unexposed regions of the layer Compositions according to the present invention may comprise inter alia heat and light stabilisers, colouring pigments and particulate filler materials, e.g. chalk, calcium carbonate, talc, mica, carbon black and glass.

Where curing of compositions according to the present invention is initiated by an initiator composition, particularly a photo-initiator composition, the concentration thereof in the composition may be in the range 0.01% to 10% by weight. For example, for permanant dry film resists the concentration of the photo-initiator composition in the composition may be in the range 1% to 10% by weight; for dental materials the concentration of the photo-initiator composition in the composition may be in the range 0.1% to 4.0% by weight.

It will be appreciated that where photo-initiator compositions are mixed with compositions according to the present invention to prepare photo-polymerisable compositions the part of the preparation of photo-polymerisable compositions in which the photo-initiator composition is added, and subsequent manipulations, e.g. preparation of a film or paste, should be carried out in the substantial absence of the electro-magnetic radiation to which the photo-intiator composition is sensitive.

Whilst various additives, e.g. fillers, reinforcing materials or inert diluents, may be present in the compositions according to the present invention which comprise photo-initiator compositions it will be appreciated that where such additives are present they are such that they do not unduly diminish the transparency or translucency of the compositions. Where the transparency or translucency of the composition is unduly diminished polymerisation thereof may be reduced or prevented.

According to a further aspect of the present invention there is provided a process for the preparation of oligomers used in compositions according to the present invention which process comprises at least the step of reacting one or more suitable aromatic compounds at least one of which has the general formula $Ar—X—Y^1$, wherein $Ar^1$, X and $Y^1$ have the meanings hereinbefore ascribed to them, one or more aldehydes and one or more carboxylic acids in the presence of a strong acid, wherein the molar ratio of strong acid to aromatic compound is preferably at least 1:1, with the proviso that where the carboxylic acid is a polymerisable olefinically unsaturated carboxylic acid the reaction is carried out at a temperature below 90° C.

The group $Ar^1$ in the one or more suitable aromatic compounds which is used in the process according to the present invention may be, for example, fused polynuclear, e.g. as in naphthlene or anthracene; or $Ph-Y^2-Ph$ in which Ph is the phenyl group and $Y^2$ has the meaning hereinbefore ascribed to it; or preferably mononuclear, e.g. as in benzene. The aromatic compound may have substituents as hereinbefore described.

Where the group $Y^1$ in the aromatic compound used in the process according to the present invention contains a suitably activated aromatic group we do not exclude the possibility that a portion thereof may be incorporated into the oligomer backbone.

Where more than one aromatic compound is used in the process according to the present invention, which aromatic compounds have different reactivities from each other in the aforesaid process, and it is desired that an oligomer of substantially uniform composition is prepared therefrom then the concentrations of the aromatic compounds in the reaction mixture must be kept in balance throughout the reaction, e.g. not all of the more reactive aromatic compound must be present at the start of the reaction. For example, phenoxyacetic acid reacts far more rapidly with formaldehyde under the reaction conditions than diphenyl ether does, thus in order to obtain a substantially uniform oligomer which contains phenoxyacetic acid residues and diphenyl ether residues, the diphenyl ether may be present at the start of the reaction and the phenoxy acetic acid added continuously or by phased addition throughout the reaction.

Where more than one aromatic compound is used in the process according to the present invention, which aromatic compounds have substantially the same reactivity as each other in the aforesaid process, and it is desired that an oligomer of substantially uniform composition is prepared therefrom the concentrations of the aromatic compounds in the reaction mixture may be the same throughout the reaction. For example, where phenoxybenzoic acid and diphenyl ether are used in the reaction, all of both reagents may be present at the start of the reaction.

As examples of aldehydes which may be used in the process according to the present invention may be mentioned inter alia benzaldehyde, tolualdehyde, phenylacetaldehyde or preferably a lower alkyl aldehyde, e.g. acetaldehyde and propionaldehyde. More preferably, however, the aldehyde is formaldehyde.

Whilst we do not exclude the possiblity that a solution of formaldehyde in, for example, water or methanol, may be used in the process according to the present invention, preferably the formaldehyde is in a solid form, e.g. paraformaldehyde, or trioxane.

The one or more carboxylic acids used in the process according to the present invention is (are) a hydrocarbyl carboxylic acid, which hydrocarbyl group may have one or more substituents and may be an alkyl, aryl, alkaryl, aralkyl or preferably an alkylene group. Examples of suitable carboxylic acids have been hereinbefore described.

As examples of strong acids which may be used in the process according to the present invention may be mentioned inter alia phosphoric acid, p-toluenesulphonic acid, trifluoromethane sulphonic acid, dichloroacetic acid, trifluoroacetic acid or preferably sulphuric acid. It will be appreciated that where the carboxylic acid used in the reaction is a strong acid a portion thereof may serve as the strong acid.

In the process according to the present invention 1 mole of one or more aromatic compounds are treated with about 1.0 to 15 moles of one or more aldehydes, about 5 to 40 moles of one or more carboxylic acids, and about 1 to 20 moles of strong acid. If too much strong acid is used it is difficult to control the exotherm and gelation occurs.

The reaction mixture used in the process according to the present invention may include water. The water may be added as a discrete component of the reaction mixture or, where one of the reactants in the reaction mixture is used in the form of an aqueous solution, e.g. formalin and 85% sulphuric acid, at least a portion of the water is added as the solvent in the solution. The total amount of water added to the reaction mixture is typically less than 100 moles per mole of the one or more aromatic compounds.

Conveniently the one or more aromatic compounds may be added to a mixture of the other reactants or the one or more aldehydes may be added to a mixture of the other reactants.

A suitable inert diluent, e.g. 1,2-dichloroethane, or dioxan, may be present in the reaction mixture to increase the solubility of the one or more aromatic compounds therein. There is a tendency for such reaction mixtures to emulsify and hence the presence of a suitable inert diluent is often not preferred.

Where no inert diluent is present the process according to the present invention is preferably carried out between 40° C. and 90° C., more preferably at a temperature between 50° C. and 60° C.

The process according to the present invention may be carried out for between a few minutes and twenty-four hours. Often substantially all the one or more aromatic compounds has reacted within a couple of hours. It will be appreciated that the reation time will depend on inter alia the reactivity of the aromatic compound in the reaction, the concentration and strength of the strong acid and carboxylic acid and the reaction temperature.

When reaction is judged to be complete the product is treated to remove at least substantially all the strong acid. The presence of residual strong acid can lead to the production of undesirable side products, with consequent decrease in properties, during production of a cured resin from the oligomer. Removal of the strong acid is conveniently effected by separating the inorganic phase from the organic phase and washing the organic phase with water, preferably hot water, until neutral. Alternatively, the reaction mixture may be dissolved in dilute base, e.g. 2% w/w aqueous sodium carbonate, and reprecipitated by addition of an appropriate amount of a strong acid, e.g. hydrochloric acid.

The invention is now illustrated by the following Examples.

In the Examples:

Number average and weight average molecular weights were determined by gel permeation chromatography on a Waters Liquid Chromatograph fitted with Styragel (Registered Trade Mark) columns;

EXAMPLE 1

This Example describes the preparation of an oligomer derived from phenoxyacetic acid and formaldehyde and having pendant and/or terminal acetoxymethyl groups.

Paraformaldehyde (1.5 grams) was added to a warm solution of p-toluenesulphonic acid hydrate (1.0 gram) and phenyoxyacetic acid (5.0 grams) in glacial acetic acid (10 grams). The reaction mixture was stirred and heated at 82° C., a clear solution formed. After 70 minutes the reaction was cooled, diluted with an equal volume of acetone and then added dropwise with stirring to distilled water (100 mls), a precipitate formed. The precipitate was washed with warm water and further purified by dissolving in aqueous 5% sodium carbonate and reacidified with acetic acid, washing with water and dissolving in acetone. The acetone solution was dried over molecular sieve, filtered and the acetone removed under vacuum. The resulting product (3.2 grams) was a transparent semi-solid which was soluble in acetone, dilute sodium carbonate solution, isopropanol and ethyl acetate and insoluble in methylene chloride, chloroform and xylene.

EXAMPLE 2

This Example describes the preparation of an oligomer derived from phenoxyacetic acid and formaldehyde and having pendant and/or terminal methacryloxymethyl groups.

Parafomaldehyde (1.4 grams) was added to a warm solution of p-toluenesulphonic acid hydrate (1.0 gram) and phenoxyacetic acid (5.0 grams) in methacrylic acid (10 grams; containing 150 ppm p-methoxyphenol). The reaction mixture was stirred and heated from 56° C. to 78° C. over 10 minutes, a clear solution formed. The solution was stirred at 80° C. for 60 minutes, then cooled and added with stirring to an excess of distilled water. A viscous oil was obtained which was washed with warm water (2×50 ml) and then worked up as in Example 1. The product (2.9 grams) was a transparent viscous liquid, soluble in dioxan and tetrahydrofuran and insoluble in chloroform. Gel permeation chromatography in dioxan using a Water G.P.C. apparatus equipped with Ultrastyragel$^R$ columns of 500A and 10$^3$A pore size indicated that the product was oligomeric with a number average molecule weight of 1200 and no detectable phenoxyacetic acid.

A sample of the product was mixed with 0.8 w/w % camphorquinone and 1.6% w/w dimethylaminoethyl methacrylate and the mixture was exposed to a 200 w low pressure mercury discharge lamp at a distance of 30 centimeters for 10 minutes. A rubbery product was obtained.

EXAMPLE 3

This Example describes the preparation of an oligomer derived from phenoxyacetic acid and formaldehyde and having pendant and/or terminal methacryloxymethyl groups.

A mixture of paraformaldehyde (3.2 grams), phenoxyacetic acid (10 grams), methacrylic acid (30.5 grams) and p-toluenesulphonic acid (1 8 grams), containing 150 ppm p-methoxyphenol, was stirred and heated from 68° C. to 76° C. over 20 minutes The reaction mixture was kept at 76° C. for a further 45 minutes, cooled and added to distilled water (200 mls), a pale yellow oil separated. The oil was dissolved in dilute aqueous sodium carbonate solution, the solution was filtered, and added dropwise with stirring to excess dilute hydrochloric acid, an oil separated out which was worked up as in Example 2. The product was a pale-yellow, transparent viscous oil which was soluble in dioxan, acetic acid, dimethyl formamide and dimethyl sulphoxide.

Proton and C$^{13}$ nuclear magnetic resonance spectroscopy indicated the presence of methacryloxymethyl groups, diaryl methylene groups, aromatic protons and oxyacetic acid groups.

EXAMPLE 4

This Example illustrates the preparation of an oligomer of phenoxyacetic acid and formaldehyde having pendant and/or terminal acryloxymethyl groups.

Phenoxyacetic acid (10 grams), acrylic acid (22 grams), p-toluenesulphonic acid hydrate (1.1 gram), paraformaldehyde (3.2 grams) and p-methoxyphenol (0.01 grams) were stirred at 80° C. until a clear solution formed. The reaction temperature was allowed to fall to 50° C. over 90 minutes. p-Methoxyphenol (0.01 grams) was added, the reaction mixture was heated to 72° C. for a further 90 minutes and was then cooled. The reaction mixture was poured into distilled water, an oil separated which was washed with warm water (2×), dissolved in dilute carbonate solution and then recovered by precipitation from excess dilute hydrochloric acid. The product was then worked up as in Example 2. The product was a pale-yellow colourless oil which was soluble in dioxan, and acetic acid and insoluble in methylene chloride. Gel permeation chromatography indicated the presence of a trace amount of acrylic acid and an oligomer of $M_n$ of approximately 900.

A sample of the product was subjected to UV radiation as described in Example 2. A tack-free product was obtained after 30 minutes exposure.

EXAMPLES 5-7

These Examples illustrate the preparation of oligomers derived from phenoxyacetic acid, diphenyl oxide, and formaldehyde and having pendant and/or terminal acryloxymethyl groups in which the molar ratio of phenoxyacetic acid to diphenyl oxide is about 1:1.

General Procedure

Distilled water, 98% sulphuric acid and paraformaldehyde were stirred and heated at 80° C. until a clear solution was obtained. The solution was cooled to 40°-52° C. and a mixture of phenoxyacetic acid and diphenyl oxide in acrylic acid was added over seconds with stirring. The temperature was allowed to fall to 40° C. over 30 minutes. A thick oily precipitate formed. The precipitate was separated, washed with warm water (2×), and dissolved in ethyl acetate (70 mls). The solution was filtered, washed with water (2×) and poured into methanol. The semi-solid precipitate which formed was washed thoroughly with distilled water, dissolved in ethyl acetate or acetone, the solution was dried over a molecular sieve and then evaporated to dryness. The product was soluble in dioxan and dilute sodium carbonate solution.

Samples of the product in acetone or ethyl acetate were mixed with a suitable catalyst, cast as films on glass, covered with "Melinex" (RTM) film and exposed to UV radiation as described in Example 2. The cured films were resistant to acetone and warm sodium carbonate sodium.

The results are given in Table 1.

TABLE 1

| Example No. | Distilled Water (mls) | 98% Sulphuric Acid (mls) | Paraform-aldehyde (g) | Diphenyl Oxide (g) | Phenoxy-acetic Acid (g) | Acrylic Acid (g) | $M_n$ | $M_w$ | Time to cure (minutes) |
|---|---|---|---|---|---|---|---|---|---|
| 5 | 28.8 | 32.0 | 8.4 | 6.5 | 6 | 30$^b$ | a | a | 3$^d$ |
| 6 | 87 | 96 | 20 | 19.5 | 18 | 105$^c$ | 527 | 2627 | 5$^e$ |

TABLE 1-continued

| Example No. | Distilled Water (mls) | 98% Sulphuric Acid (mls) | Paraform- aldehyde (g) | Diphenyl Oxide (g) | Phenoxy- acetic Acid (g) | Acrylic Acid (g) | $M_n$ | $M_w$ | Time to cure (minutes) |
|---|---|---|---|---|---|---|---|---|---|
| 7 | 216 | 240 | 80 | 65 | 60 | 315 | 850 | 2700 | a |

<sup>a</sup>Not determined.
<sup>b</sup>Containing 0.02 gram p-methoxyphenol.
<sup>c</sup>Containing 0.04 gram p-methoxyphenol.
<sup>d</sup>3% Irgacure 184.
<sup>e</sup>4% Irgacure 184.

EXAMPLE 8

This Example illustrates the preparation of an oligomer derived from 3-ohenoxybenzoic acid and formaldehyde and having pendant and/or terminal methacryloxymethyl groups.

A mixture obtained by adding paraformaldehyde (2.0 grams; 0.066 moles) to a mixture of distilled water (7.2 grams) and 98% sulphuric acid (14.7 grams; 8.0 mls) was heated with stirring until a clear solution was obtained. The solution was cooled to 57° C. and a solution of 3-phenoxybenzoic acid (5.0 grams; 0.023 moles; m.p. 149°–150° C.) and methoxyphenol (50 milligrams) in methacrylic acid (15.23 grams; 15 mls) was added with vigorous stirring. The reaction temperature was increased to 68° C. and maintained thereat for 2.75 hours, when gel permeation chromatography indicated that all the 3-phenoxybenzoic acid had been consumed The reaction mixture was poured into distilled water (200 mls) with vigorous stirring and a viscous oil separated. The oil was washed with hot water (50 mls X 4), then dissolved in chloroform (40 mls) and the solution was dried over molecular sieves, filtered and evaporated on a rotary evaporator at 50° C. under vacuum to leave a product in the form of a transparent pale-yellow viscous liquid (4.8 grams).

The product dissolved readily in 5% aqueous sodium bicarbonate solution and could be reprecipitated unchanged (as indicated by gel permeation chromatography) on acidification of the solution with dilute hydrochloric acid.

A 50% w/w solution (containing 6% (based on oligomer) "Irgacure" 484) of the product in methyl ethyl ketone was poured onto glass plates and the solvent evaporated off to leave a layer of oligomer. On exposure to a U.V. lamp for two minutes a tough hard film was obtained from the layer.

EXAMPLE 9

This Example illustrates the preparation of an oligomer derived from 2-phenoxybenzoic acid and formaldehyde and having pendant and/or terminal methacryloxymethyl groups.

A solution of paraformaldehyde (3.0 grams; 0.10 moles) in distilled water (14.4 grams) and 98% sulphuric (29.4 grams; 16.0 mls), prepared as in Example 8, was stirred at 68° C. while a mixture of 2-ph-enoxybenzoic acid (10 grams; 0.047 moles) in methacrylic acid (30.5 grams; 30 mls) was added. The reaction mixture was stirred vigorously at approximately 65° C. for 1.33 hours. It was then found by gel permeation chromatography that the 2-phenoxybenzoic acid had been consumed. The reaction mixture was cooled, the upper viscous liquid layer was separated, and washed repeatedly with warm water to leave a semi-solid product (8.2 grams) which was soluble in chloroform, methyl ethyl ketone and dilute sodium bicarbonate solution.

EXAMPLE 10

This Example illustrates the preparation of an oligomer derived from 2-ph-enoxybenzoic acid, diphenyl ether and formaldehyde and having pendant and/or terminal methacryloxymethyl groups in which the molar ratio of 2-phenoxybenzoic acid to diphenyl ether is about 1:1.

A solution of paraformaldehyde (48 grams; 1.6 moles) in distilled water (172.8 grams) and 98% sulphuric acid (353.3 grams), prepared as in Example 8, was stirred vigorously at 50° C. and a solution of 2-phenoxybenzoic acid (66 grams) and diphenyl ether (54 grams) in methacrylic acid (365 grams) containing p-methoxyphenol (0.05 grams) was added. The temperature of the reaction mixture was allowed to fall to 43° C. over 2.67 hours by which time all the 2-phenoxybenzoic acid and the diphenyl ether had been converted into oligomer, as shown by gel permeation chromatography. The reaction mixture was allowed to stand. An upper viscous liquid layer was separated and washed repeatedly with warm water and then with a 1:1 mixture of methanol and water and then dissolved in chloroform. The solution was dried over a molecular sieve and then evaporated.

The product was found to have $M_n=488$, $M_w=1902$ (by gel permeation chromatography), an acid value of 70.2 milligrams KOH/gram of product (by titration against KOH solution) and a functionality of 2.3 methacrylate groups/molecule (saponification).

EXAMPLES 11–13

These Examples illustrate the preparation of oligomers derived from .phenoxyacetic acid, diphenyl ether and formaldehyde and having pendant and/or terminal acryloxymethyl groups. In Example 11, the molar ratio of phenoxyacetic acid to diphenyl ether is about 2:5. In Examples 12 and 13, the molar ratio of -phenoxyacetic acid to diphenyl ether is about 2:3.

General Procedure

A hot solution of paraformaldehyde in distilled water and 98% sulphuric acid, prepared as in Example 8, was stirred vigorously while a first portion of acrylic acid was added. The temperature of the resulting solution dropped to a First Temperature. A mixture of diphenyl ether, a second portion of acrylic acid and a first portion of phenoxyacetic acid was added to the solution. A second portion of phenoxyacetic acid was then added batchwise over a predetermined time (Addition Time). During the addition the temperature of the reaction was allowed to rise to the Reaction Temperature and was maintained at this temperature with stirring for a predetermined time (Reaction Time). Stirring was then stopped and the reaction mixture was allowed to stand. An upper liquid layer was separated, washed with warm water (2 liters), and dissolved in chloroform or methylene chloride (1 liter). The solution was washed repeatedly with water until the washings were neutral, dried over molecular sieves, filtered and evaporated.

The amounts of starting materials and the reaction conditions are shown in Table 2. The physical state and the gel permeation chromatographic analysis of the product are given in Table 3.

The product from Example 12 was soluble in chloroform, methyl ethyl ketone, and dilute aqueous sodium carbonate solution.

The product from Example 13 had an acid value of 61.4 mgms KOH/gram.

TABLE 4

|  | Flexural Strength MPa | Flexural Modulus GPa |
| --- | --- | --- |
| Initial | 84.1 | 2.09 |
| 20 Days storage | 82.3 | 2.30 |
| 105 Days storage | 78.9 | 2.53 |

EXAMPLE 15

This Example illustrates the preparation of photoresists from compositions according to the present invention.

An approximately 50% w/w solution of an oligomer prepared as in Example 7 and Irgacure (RTM) 651 was

TABLE 2

| Ex No. | $CH_2O^a$ (grams) | PhOCH$_2$CO$_2$H (grams) First Portion | PhOCH$_2$CO$_2$H (grams) Second Portion | DPE$^b$ (grams) | 98% H$_2$SO$_4$ (mls) | Water (grams) | Acrylic acid (mls) First Portion | Acrylic acid (mls) Second Portion | First Temperature (°C.) | Addition Time (minutes) | Reaction Temperature | Reaction Time (minutes) |
| --- | --- | --- | --- | --- | --- | --- | --- | --- | --- | --- | --- | --- |
| 11 | 61 | 3 | 31 | 94 | 320 | 290 | 300 | 2 | 62 | 6 | 52–55 | 25 |
| 12 | 77 | 2 | 57.6 | 100 | 320 | 290 | 245 | 5 | 40 | 5 | 63 | 25 |
| 13 | 77 | 2 | 57.6 | 100 | 201 | 181 | 345 | 5 | 42 | 5 | 64 | 20 |

$^a$As paraformaldehyde.
$^b$Diphenyl ether.

TABLE 3

| Example No | Physical State | Number Average Molecular Weight$^a$ | Weight Average Molecular Weight$^a$ | Functionality |
| --- | --- | --- | --- | --- |
| 11 | Viscous liquid | 603 | 2030 | 3.2 |
| 12 | Low Softening Solid | 884 | 8400 | b |
| 13 | Viscous liquid | 581 | 1666 | 3.7 | a: Determined by gel permeation chromatography
b: Not determined

EXAMPLE 14

This Example illustrates the preparation of cured products from a composition according to the present invention.

A sample (10 grams) of the oligomer prepared in Example 11 was mixed with camphorquinone (0.08 grams), N,N-dimethylaminoethyl methacrylate (0.16 grams) and t-butyl perbenzoate (0.08 grams) and polymerised by exposure to light from a 200 watt low pressure mercury lamp for 3 hours. A stiff, transparent plaque was obtained which had a Young's modulus of 3.2 GPa at 25° C. and exhibited a peak of the loss process (tan delta) at 110° C.

A sample (20 grams) of the oligomer prepared in Example 11 was mixed with triethyleneglycol dimethacrylate (20 grams), camphorquinone (0.28 grams) and dimethylaminoethyl methacrylate (0.2 grams) (hereinafter referred to for convenience as "Mixture A"). Portions of the mixture were poured into moulds of dimensions 25 mm×2 mm×2 mm and cured by exposure to visible light for 30 seconds.

The flexural properties of the cured products were determined both before and after storing in water at 37° C. The results are given in Table 4.

coated onto a Melinex (RTM) support film (23 microns thick) using a wire-wound coating bar to give a wet film of thickness of about 125 microns. The wet film was dried with a hot air blower and allowed to stand for 24 hours, it was then tack-free and had a thickness of about 30 microns. The tack free layer contained 6.5% w/w Irgacure (RTM) 651.

The bare surface of the layer was contacted with the epoxy surface of a standard single-sided epoxy board used in the electronics industry (FR-4 epoxy glass) (which had been scrubbed under water with Scotch-Brite (RTM) and dried) and laminated thereto using a Dynachem (RTM) Model 300 laminator at 100° C. and a throughput of 1.5 feet per minute. A laminate was obtained which comprised a board, a layer of a composition according to the present invention and a support film.

A first portion of the laminate was exposed, through a Stouffer 21-step sensitivity guide disposed on the surface of the support film, to UV radiation, from a "Countess" (ex Parker Graphics Limited) exposure unit provided with two MLV 300w Philips UV lamps, for 12 minutes. It was stored for 30 minutes at room temperature, the support film was removed and it was washed in 2% aqueous sodium carbonate solution for 4 minutes at room temperature in an ultrasonic bath and then rinsed in water. A cured resin which was resistant to washing was obtained up to and including step 12.

A second portion of the laminate was exposed and developed as above except that the Stouffer guide was replaced by a standard photo-tool having approximately 300 micron lines and spaces and exposure lasted for 12 minutes. A resist bearing a pattern of about 300 micron lines and spaces was obtained.

A third portion of the laminate was exposed for 12 minutes as described for the first portion except that the Stouffer guide was omitted. One half of the resist was post-cured by heating at 160° C. for 30 minutes and the other half by heating at 160° C. for 30 minutes followed by exposure to UV light for 2 hours using a Philips HPR 125w mercury discharge lamp at a distance of 40 centimeters.

The two post-cured halves were subjected to caustic soda solution at pH 11.7 and 80° C. for 2.5 hours. No visible change occurred in the resist layers.

EXAMPLE 16

This Example illustrates the use of a composition according to the present invention as an adhesion promoter for a dental filling.

Surfaces were cut in human molars freshly extracted under a general anaesthetic, each surface was cut with a well irrigated diamond saw. The surfaces were cut in the lower third of dentine nearest the pulp and in the upper third of dentine nearest the enamel.

Portions of Mixture A prepared in Example 14 were spread on the freshly prepared surfaces and separately cured by exposure for 20 seconds under a "Luxor Light" (ex Imperial Chemical Industries PLC). Samples of "Occlusin" dental filling composition (ex Imperial Chemical Industries PLC) were spread on the cured adhesion promoter and cured by exposure for 2 minutes under a "Luxor Light" to give cured dental fillings measuring approximately 2 mm×2 mm×1 mm.

We claim:

1. A composition comprising an oligomer, which is linear or branched, which
   (a) comprises on average at least one in-chain residue of the general formula

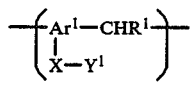

and;
   (b) has one or more pendant and/or terminal acyloxymethyl groups;
   wherein $Ar^1$ is an aromatic group or a substituted aromatic group;
   $R^1$ is hydrogen or a hydrocarbyl group;
   X is a group which activates $Ar^1$ to electrophilic attack; and
   $Y^1$ is an organic residue bearing a carboxyl substituent.

2. A composition as claimed in claim 1 wherein the oligomer comprises one or more residues of the general formula

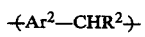

wherein
   $Ar^2$, which is the same as or different from $Ar^1$, is an aromatic group or a substituted aromatic group; and
   $R^2$, which is the same as or different from $R^1$, is hydrogen or a hydrocarbyl group.

3. A composition as claimed in claim 1 wherein $Ar^1$ is mononuclear.

4. A composition as claimed in claim 2 wherein $Ar^2$ has the structure —φ—$Y^2$—φ— wherein φ is the phenylene group; and $Y^2$ is a direct link between two phenylene groups, or a divalent residue which includes one or more in-chain atoms, each of which atoms carbon or a hetero atom and one or more atoms appendant thereto.

5. A composition as claimed in claim 4 wherein $Y^2$ is oxygen.

6. A composition as claimed in claim 2 wherein the molar ratio of the residue

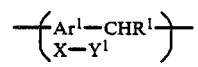

to the residue

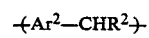

is between 3:1 and 1:3.

7. A composition as claimed in claim 1 wherein X is oxygen

8. A composition as claimed in claim 1 wherein $Y^1$ is

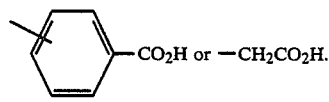

9. A process for the preparation of an oligomer as defined in claim 1 which process comprises at least the step of reacting one or more suitable aromatic compounds at least one of which has the general formula Ar′—X—$Y^1$, wherein Ar′, X and $Y^1$ have the meanings ascribed to them in claim 1, one or more aldehydes and one or more carboxylic acids in the presence of a strong acid, with the proviso that where the carboxylic acid is a polymerisable olefinically unsaturated carboxylic acid the reaction is carried out at a temperature below 90° C.

10. A composition comprising an oligomer, which is linear or branched, which
    (a) comprises on average at least one in-chain residue of the general formula

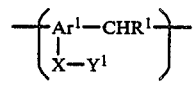

and;
    (b) has one or more pendant and/or terminal acyloxymethyl groups;
    wherein $Ar^1$ is an aromatic group or a substituted aromatic group;
    $R^1$ is hydrogen or a hydrocarbyl group;
    X is a group which activates $Ar^1$ to electrophilic attack; and
    $Y^1$ is an organic residue bearing a carboxyl substituent; where the acyloxy group in the one or more pendant and/or terminal acyloxymethyl groups is derived from a polymerisable olefinically unsaturated carboxylic acid.

11. A composition as claimed in claim 10, wherein the polymerisable olefinically unsaturated carboxylic acid is acrylic acid or methacrylic acid.

12. A composition comprising an oligomer, which is linear or branched, which
    (a) comprises on average at least one in-chain residue of the general formula

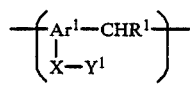

and;
(b) has one or more pendant and/or terminal acyloxymethyl groups;
wherein $Ar^1$ is an aromatic group or a substituted aromatic group;
$R^1$ is hydrogen or a hydrocarbyl group;

X is a group which activates $Ar^1$ to electrophilic attack; and
$Y^1$ is an organic residue bearing a carboxyl substituent; and
an additional polymerizable olefinically unsaturated monomer which is copolymerizable with said oligomer, the acyloxy group being derived from a polymerisable olefinically unsaturated carboxylic acid.

13. A composition as claimed in claim 12 wherein the said monomer is an acrylate or methacrylate ester.

* * * * *